United States Patent
Mayer et al.

[11] Patent Number: 5,983,708
[45] Date of Patent: Nov. 16, 1999

[54] GRAVIMETRIC CUP

[75] Inventors: Daniel W. Mayer, Wyoming; Michelle T. Stevens, Minneapolis, both of Minn.

[73] Assignee: Mocon, Inc., Minneapolis, Minn.

[21] Appl. No.: 09/124,257

[22] Filed: Aug. 3, 1998

[51] Int. Cl.[6] .......................... G01N 15/08; G01N 27/46; G01M 3/26
[52] U.S. Cl. ................................ 73/38; 73/64.47; 73/73; 73/866
[58] Field of Search .............................. 73/38, 52, 64.47, 73/865.6, 866, 73

[56] References Cited

U.S. PATENT DOCUMENTS

| | | | |
|---|---|---|---|
| 3,195,346 | 7/1965 | Ehrmantraut et al. | 73/53 |
| 3,466,925 | 9/1969 | Ziegenhagen et al. | 73/38 |
| 3,572,090 | 3/1971 | Graham et al. | 73/73 |
| 3,577,767 | 5/1971 | Stedile | 73/38 |
| 3,590,634 | 7/1971 | Pasternak et al. | 73/159 |
| 3,635,075 | 1/1972 | Gilbert | 73/64.3 |
| 4,028,931 | 6/1977 | Bisera et al. | 73/64.3 |
| 4,050,995 | 9/1977 | Bredeweg | 204/1 T |
| 4,385,517 | 5/1983 | Sorce et al. | 73/38 |
| 4,561,289 | 12/1985 | Jones | 73/38 |
| 4,715,212 | 12/1987 | Johanson | 73/38 |
| 4,862,730 | 9/1989 | Crosby | 73/38 |
| 4,918,981 | 4/1990 | Gore | 73/76 |

*Primary Examiner*—Michael Brock
*Assistant Examiner*—J. David Wiggins
*Attorney, Agent, or Firm*—Paul Sjoquist

[57] ABSTRACT

A gravimetric cup for containing a liquid sample to be measured for moisture or vapor transmission loss therefrom, such gravimetric cup having a lower cup body and a cover, the cover having an outer edge rim alignable with an upper edge rim of the cup for mounting a film membrane thereacross, and the cover having radial, upwardly curved ribs extending between the outer edge rim and a center hub region so as to provide an evenly distributed clamping force upon the membrane. The cup body has a pair of upwardly projecting posts, each having an engagement channel. A clamping bar has slotted ends for engaging against the respective post engagement channels, and a center threaded hole for receiving the threaded shank of a tightening knob that applies downward force to the cover.

6 Claims, 3 Drawing Sheets

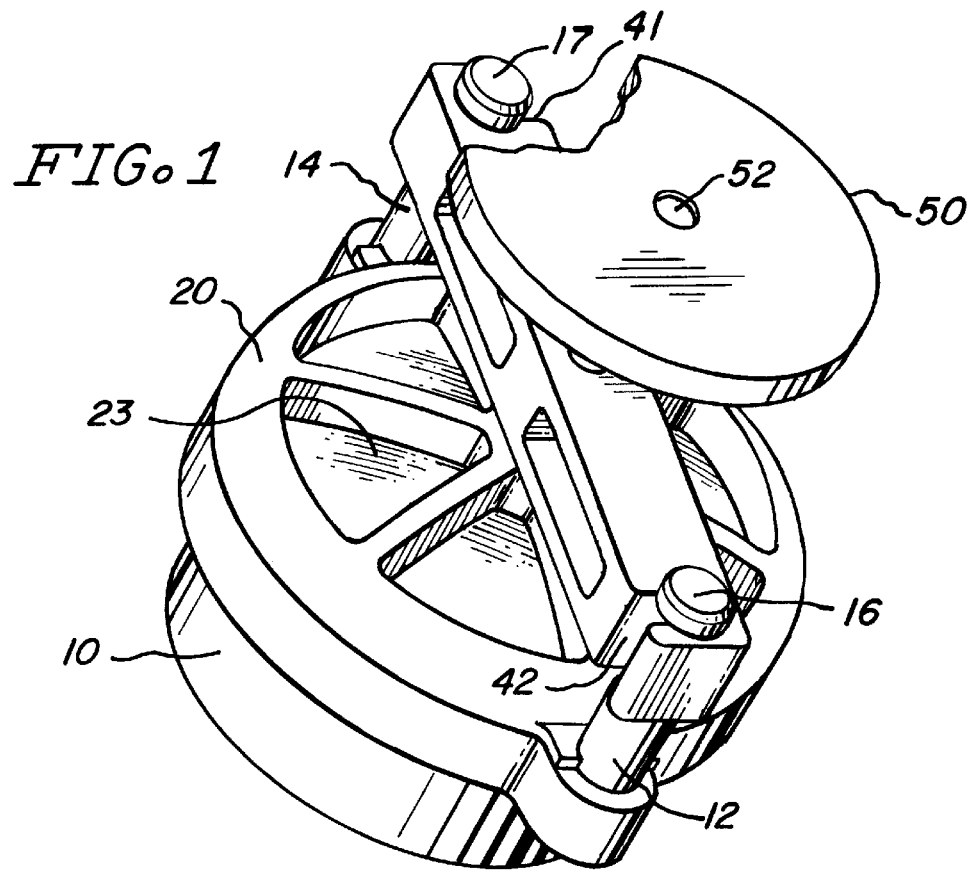
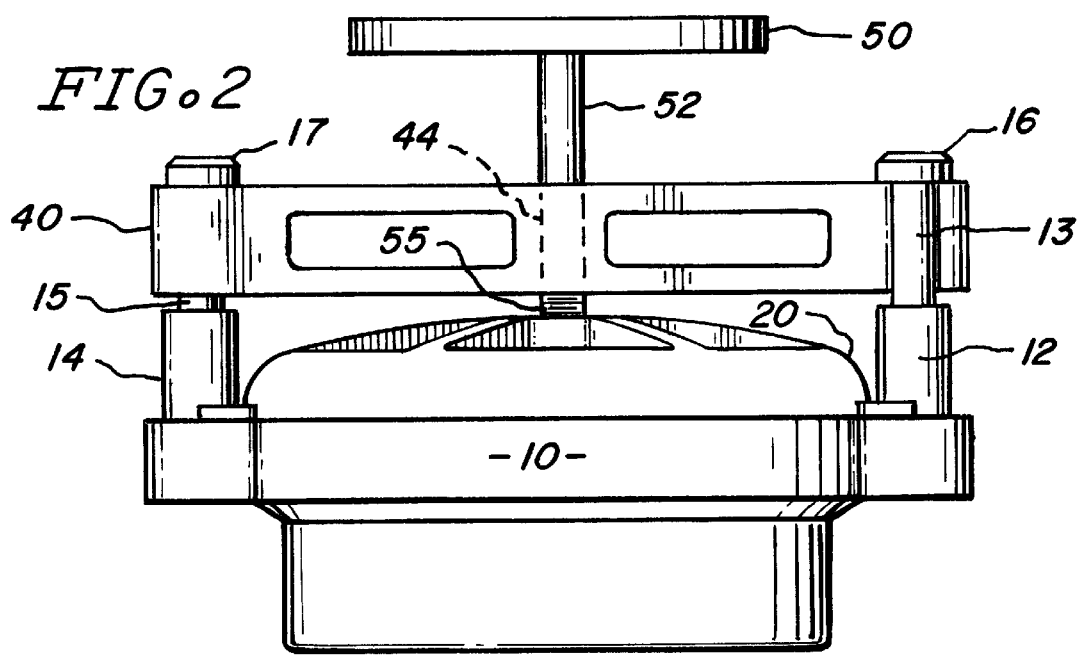

GRAVIMETRIC CUP

BACKGROUND OF THE INVENTION

The present invention relates to a method and apparatus for measuring the transmission of liquid vapors through membranes. The permeability of film membranes to moisture and other vapors is considered to be a very important factor in the ability of the membrane to act as a barrier, for sealing flavors in packaged materials and for preventing degradation of the product wrapped inside the film material. Among the types of film membrane which are used for packaging materials are plastics, coated papers and various combinations of multi-layered packaging.

One accurate technique for measuring the ability of a film material to serve as a barrier to moisture and various liquid vapors is the gravimetric technique, which involves the steps of actually weighing a closed container having an initial moisture content, where the container has a wall made from the test film material, the loss of weight over time being attributable to the loss of moisture through the wall of film material. A test device known as a Thwing-Albert test cup has long been used for this purpose. This device consists of a cup having a removable cover ring, where a film sample is clamped over the open top of the cup by the ring, and the entire assembly is periodically weighed on an accurate scale. As moisture escapes through the film material the cup loses weight, and after a period of time the total weight loss can be translated into a numeric value which represents the transmission rate of moisture through the film material. The Thwing-Albert test cup is a relatively simple device, consisting of a cover ring having a number, usually six or eight, of threaded fasteners located at equiangular positions about the ring, wherein the fasteners are threaded into the lower cup body and are used to clamp the edge of the film material tightly against the upper rim of the cup. This device is usually accurate for measuring permeation rates through film material, having an accuracy in the range of 20–100 milligrams per day with an initial permeant weight of 30–40 grams inside the cup. The device is not sufficiently accurate for measuring permeation rates at very much lower levels, for the readings are compromised by extraneous leakage due to uneven clamping of the film material, including leakage around the gasket materials used to seal the film across the top of the gravimetric cup.

As technology has progressed, the barrier capabilities of film materials have greatly improved over the years, and materials are now being developed which have permeation rates far below the range of accuracy which the Thwing-Albert test cup is capable of measuring. Weight loss accuracy of around 1–5 milligrams per day is now desirable, and test devices capable of operating with this accuracy are very much needed.

It is an object of the present invention to provide a test apparatus which enables the precise and repeatable measurement of permeation of liquid vapors through a film material below a rate of about 5 grams per day, with an accuracy of better than about one milligram per day.

SUMMARY OF THE INVENTION

The apparatus of the invention includes a test fixture which is arranged as a gravimetric cup having a removable cover for clamping a film membrane tightly over the rim of the cup. The cover is constructed in a convex shape, with a plurality of curved ribs radiating from a center region having a small recess. The cup body has a pair of clamping posts projecting upwardly adjacent the cup rim, and a clamping bar is arranged between the posts. A threaded fastener passes through the clamping bar and is urged against the center recess of the cover to clamp the cover against the rim of the cup; the film membrane is placed between the cover and the rim prior to clamping the cover over the rim and membrane. The downward force applied by the threaded fastener against the cover is advantageously equally applied, via the radiating rings of the cover, over the entire circumference of the cover, thereby eliminating any uneven clamping forces against the membrane and ensuring that all porions of the membrane are tightly clamped so as to prevent leakage.

The foregoing and other objects and advantages will become apparent from the following detailed description and claims, and with reference to the appended drawings.

BRIEF DESCRIPTION OF THE DRAWINGS

FIG. 1 shows an isometric view of the invention;

FIG. 2 shows an elevation view of the invention in a closed position for conducting test measurements;

DESCRIPTION OF THE PREFERRED EMBODIMENT

Figure 3:
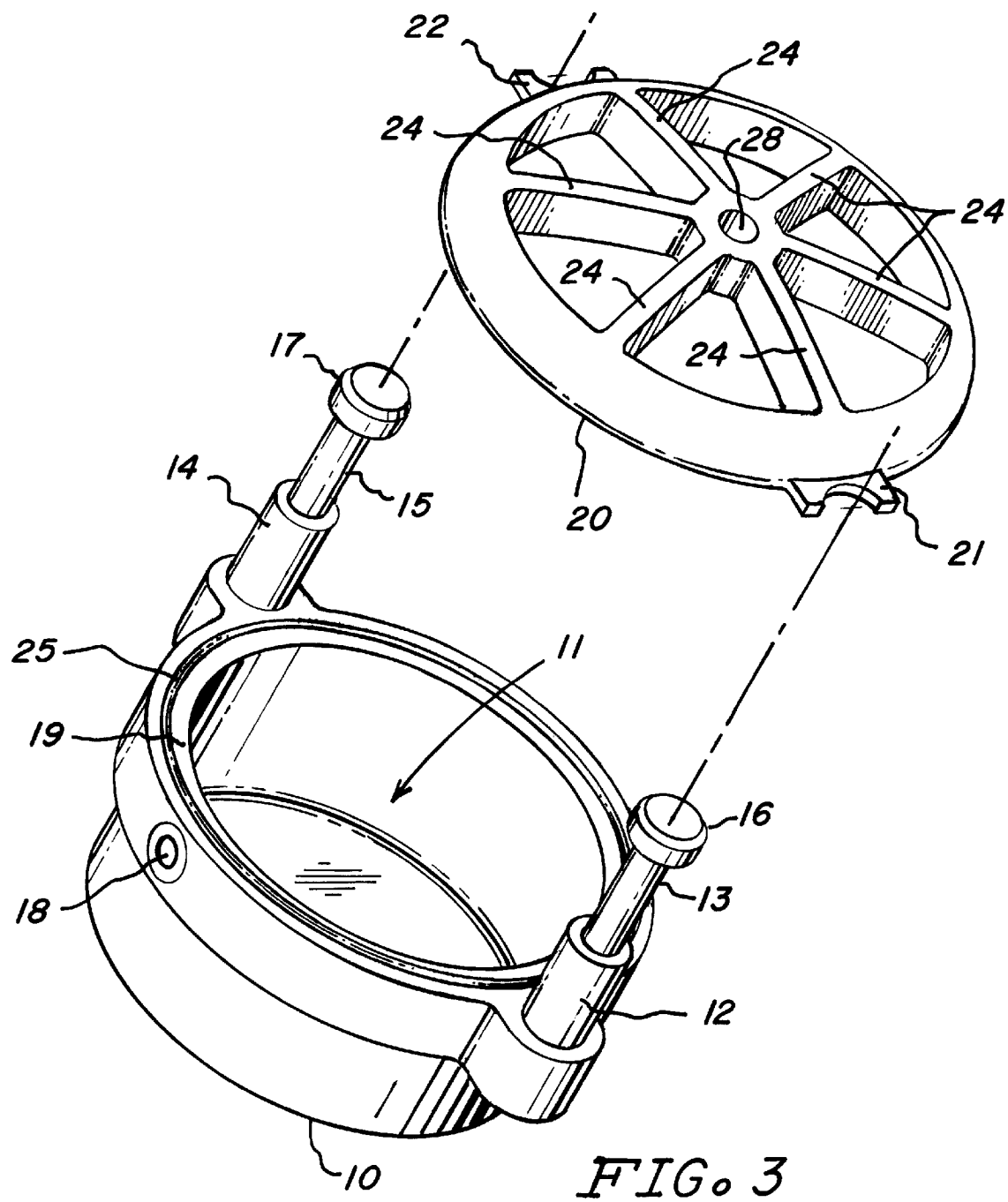
FIG. 3 shows an exploded view of the cover relative to the cup.

Referring first to FIGS. 1 and 2, there is shown an isometric view and an elevation view of the invention, wherein a cup 10 is positioned beneath a cover 20. A pair of posts 12, 14 are affixed at their respective lower ends to the cup 10. Each of the posts 12, 14 has a reduced diameter shank portion 13, 15 and an upper end cap 16, 17 which is preferably of the same diameter as the posts 12, 14. Each of the reduced diameter shank portions 13, 15 serves as an engagement channel for retaining a clamping bar 40 in a locked position.

The clamping bar 40 has a pair of slotted ends 41, 42 which are sized to fit about the reduced shank portions 13, 15, but the slotted ends 41, 42 are smaller than the upper end caps 16, 17. A threaded hole 44 passes through the center of clamping bar 40. A knob 50 having a threaded shank 52 is fitted to engage the threaded hole 44, and the lower end 55 of the threaded shank 52 engages against the center recess of cover 20. When the knob 50 is turned to loosen the threaded engagement, the clamping bar 40 may be rotated and disengaged from the respective post shank portions 13, 15, and the cover 20 may be lifted away from its seated position atop the cup 10, to remove or insert a film membrane 23.

FIG. 3 shows an exploded view of the cover 20 in alignment over the cup 10. The cover 20 has a pair of locating tabs 21, 22 having a curved slot for fitting over the posts 12, 14, to locate the cover 10 properly relative to cup 10, as indicated by the dotted lines. The cover 20 has six radial ribs 24 emanating from a central hub, and the central hub has a recess 28 for receiving the end 55 of the threaded shank 44 of the knob 50.

The cup 10 has an interior recess 11 for receiving a water sample, or a sample of some other liquid agent, and a side threaded opening 18 for receiving a relief valve such as a threaded needle valve (not shown). The relief valve is necessary to equalize pressure within and without the interior of the cup 10 after the cover has fully clamped a membrane material over the top opening of cup 10, and after whatever preheating steps have been taken, but before the weighing steps are taken. Once the pressure has been equalized at the temperature at which the weighing steps are to be taken, the relief valve is fully closed to seal the interior of the cup from any outside leakage.

The upper rim of the cup 10 has a circumferential groove 19 sized to receive an O-ring 25, which is seated prior to closing the cover 20 over the cup 10. The O-ring groove 19 is located to be in alignment with the cover 20 rim edge when the cover is fastened in clamping relationship to the cup 10. The posts 12, 14 may be threaded into the body of cup 10, or may be otherwise affixed to the body of cup 10 in a more or less permanent connection.

Figure 4:
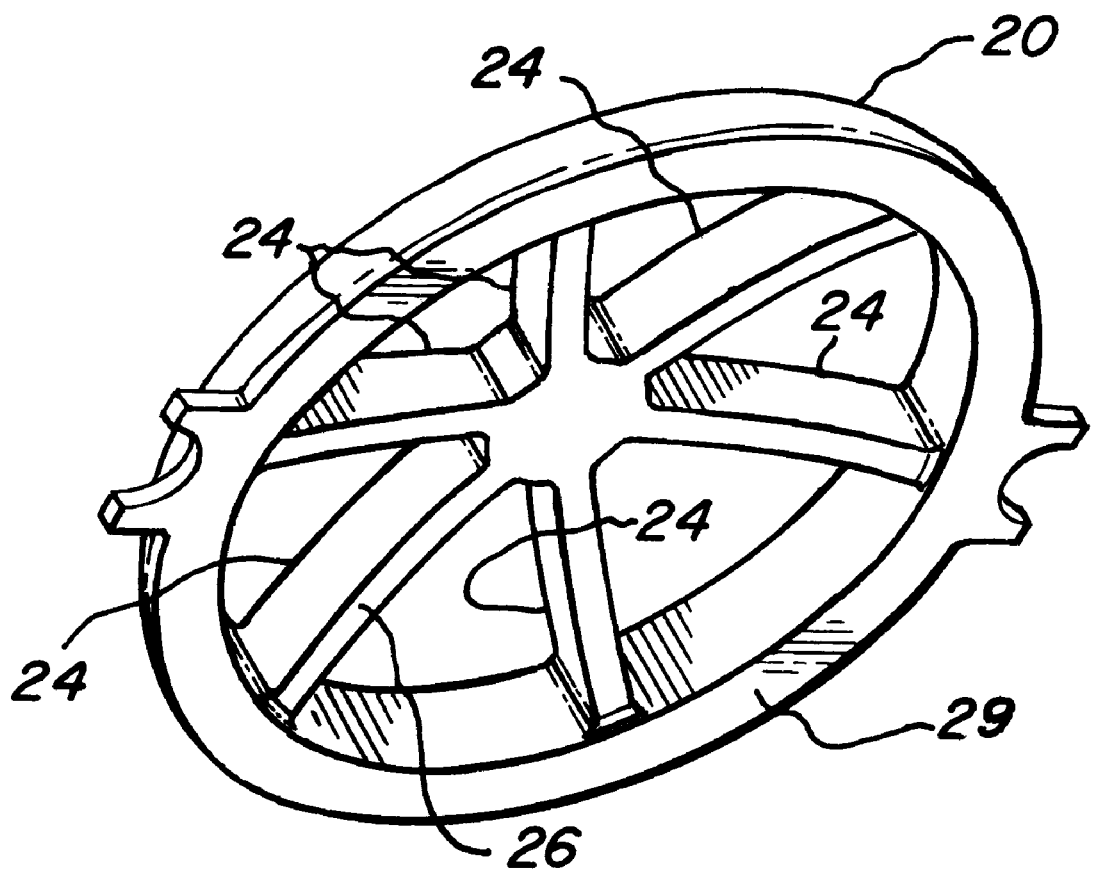
FIG. 4 shows a view of the underside of the cover.

FIG. 4 shows a view of the underside of cover 20, to illustrate the upwardly curved contour of the radiating ribs 24, relative to the cover 20 rim edge. The lower surface 29 of the cover 20 rim edge is flat and in surface alignment with the upper rim edge of cup 10, whereas the entire remaining undersurface 26 of the ribs 24 and the center hub surface is upwardly contoured, following a concave imaginary surface shape so as to elevate the ribs 24 and the center hub region away from the contact plane of the rim edge surface 29.

In operation, an O-ring 25 is seated in O-ring groove 19 and a quantity of liquid permeant is placed inside cup 10. A membrane film 23 is placed over the top opening of cup 10, and cover 20 is positioned over the membrane material in alignment with the posts 12, 14. The clamping bar 40 is rotatably located and locked about the narrowed shank portions 13, 15 of posts 12, 14, and knob 50 is turned to tighten the lower end 55 of its threaded shank 52 against the center recess 28 of cover 20, until a tight seal has been made against the film membrane. The tightening of knob 50 results in a downward force being applied against the center hub region of the cover 20, and this downward force is equally transmitted via the radial ribs 24 to the outer rim edge surface 29, and is applied equally to all circumferential portions of the membrane film material and O-ring.

The relief valve is opened until the entire cup assembly has been brought to the desired test temperature, and the relief valve is then closed. Thereafter, weight measurements are made at desired intervals to record the weight loss of the cup assembly as the liquid permeant inside the cup 10 gradually permeates through the film membrane material, and the data recorded from these measurements can be translated into a permeability coefficient for the material under test, usually expressed in terms of grams per square meter per day.

The entire cup assembly may be made from aluminum or similar material, and the initial weight of the assembly should be about 150 grams. The interior cup volume is sufficient to hold about 30–40 grams of liquid permeant. The apparatus is capable of accurately and repeatably measuring weight loss, assuming a comparable accuracy of the weighing apparatus, down to about one milligram. The unintended leakage loss will be limited to approximately 0.5 milligrams per day.

The foregoing description of a preferred embodiment of the invention is intended to be illustrative and not limiting. The true scope of the invention is to be understood and limited by the claims herein, variations in particular details of the invention being entirely possible within the overall scope of the invention as claimed.

What is claimed is:

1. A gravimetric cup apparatus for containing a liquid sample to be measured for moisture or vapor transmission loss therefrom, comprising a) a lower cup having an interior recess and an upper rim for mounting a film membrane thereacross, the upper rim having a circumferential O-ring in an O-ring groove, and a pair of posts affixed to said upper rim, said posts each having an engagement channel formed as a part thereof;

b) a cover having an outer rim edge sized for alignment against said lower cup upper rim, and having a plurality of upwardly curved radial ribs extending between said outer rim edge and a raised center hub region spaced away from said film membrane;

c) a clamping bar having slot means for engagement against said engagement channels and having a center threaded hole therethrough alignable with said center hub region when said slot means are engaged with said engagement channels; and d) a knob having a threaded shank sized for engagement with said clamping bar threaded hole, said threaded shank having a lower end alignable with said center hub region for applying a downward force to said cover so as to provide an evenly distributed clamping force upon an edge of said membrane.

2. The apparatus of claim 1, wherein said cover further comprises a pair of locating tabs alignable about said posts.

3. The apparatus of claim 2, wherein said posts each further comprise cylindrical posts.

4. The apparatus of claim 3, wherein said post engagement channels each further comprise a length of reduced diameter of said posts, between respective post portions not having a reduced diameter.

5. The apparatus of claim 4, wherein said clamping bar further comprises a generally rectangular bar having two ends, and said slot means further comprise an arcuate slot proximate each of said bar ends and sized slightly larger than said reduced diameter portions of said posts.

6. The apparatus of claim 5, wherein said cup further comprises means for providing a pressure relief between the interior of said cup and the exterior.

* * * * *